US008048682B2

(12) United States Patent
West et al.

(10) Patent No.: US 8,048,682 B2
(45) Date of Patent: Nov. 1, 2011

(54) DEVICE AND METHOD FOR DETECTING SULFUR DIOXIDE AT HIGH TEMPERATURES

(75) Inventors: David L. West, Oak Ridge, TN (US); Frederick C. Montgomery, Oak Ridge, TN (US); Timothy R. Armstrong, Clinton, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 805 days.

(21) Appl. No.: 12/111,641

(22) Filed: Apr. 29, 2008

(65) Prior Publication Data
US 2008/0297178 A1    Dec. 4, 2008

Related U.S. Application Data

(60) Provisional application No. 60/914,772, filed on Apr. 30, 2007.

(51) Int. Cl.
*G01N 30/96* (2006.01)
*G01N 7/00* (2006.01)
*G01N 33/00* (2006.01)

(52) U.S. Cl. .............................. 436/122; 422/83; 422/88

(58) Field of Classification Search .................... 422/83, 422/88; 436/122
See application file for complete search history.

(56) References Cited

U.S. PATENT DOCUMENTS

| | | | |
|---|---|---|---|
| 3,934,193 A | 1/1976 | Hall | |
| 4,440,726 A | 4/1984 | Coulson | |
| 4,622,105 A | 11/1986 | Liu et al. | |
| 5,985,673 A | 11/1999 | Bao et al. | |
| 6,165,251 A | 12/2000 | Lemieux et al. | |
| 6,165,336 A * | 12/2000 | Maki et al. ..................... | 204/415 |

(Continued)

FOREIGN PATENT DOCUMENTS

GB    1382640    2/1975

OTHER PUBLICATIONS

"Gas Sensors for Fossil Energy Applications" Armstrong, T., et al., Presentation at the 20th Annual Fossil Energy Conference, Knoxville, TN, 1-31 (Jun. 13, 2006) http://www.ms.ornl.gov/FEM20/presentations/FE2006/Tuesday/ArmstrongT.ppt.

(Continued)

*Primary Examiner* — Lore Jarrett
(74) *Attorney, Agent, or Firm* — Scully, Scott, Muphy & Presser, P.C.

(57) ABSTRACT

The present invention relates to a method for selectively detecting and/or measuring gaseous $SO_2$ at a temperature of at least 500° C., the method involving: (i) providing a $SO_2$-detecting device including an oxygen ion-conducting substrate having on its surface at least three electrodes comprising a first, second, and third electrode; (ii) driving a starting current of specified magnitude and temporal variation between the first and second electrodes; (iii) contacting the $SO_2$-detecting device with the $SO_2$-containing sample while maintaining the magnitude and any temporal variation of the starting current, wherein said $SO_2$-containing sample causes a change in the electrical conductance of said device; and (iv) detecting the change in electrical conductance of the device based on measuring an electrical property related to or indicative of the conductance of the device between the first and third electrodes, or between the second and third electrodes, and detecting $SO_2$ in the $SO_2$-containing sample based on the measured change in electrical conductance.

44 Claims, 4 Drawing Sheets

U.S. PATENT DOCUMENTS

| | | | |
|---|---|---|---|
| 6,309,612 B1 | 10/2001 | Balachandran et al. | |
| 6,355,150 B1 | 3/2002 | Savin-Poncet et al. | |
| 6,598,596 B2 | 7/2003 | Wachsman et al. | |
| 6,716,327 B1 * | 4/2004 | De La Prieta et al. | 204/426 |
| 2001/0052459 A1 | 12/2001 | Essalik et al. | |
| 2004/0033414 A1 * | 2/2004 | Rohrl | 429/46 |
| 2005/0173265 A1 | 8/2005 | Stahl | |
| 2006/0073070 A1 | 4/2006 | Montgomery et al. | |
| 2006/0131182 A1 | 6/2006 | Mazanec et al. | |
| 2007/0289870 A1 * | 12/2007 | Nair et al. | 204/424 |

OTHER PUBLICATIONS

"Gas Sensors for Fossil Energy Applications" Armstrong, T., et al., Presentation at Oak Ridge National Laboratory, Knoxville, TN, 1-20, (May 2, 2007).

Miura, N., et al., "High-Temperature Potentiometric/Amperometri $No_x$ Sensors Combining Stabilized Zirconia With Mixed-Metal Oxide Electrode" *Sensors and Actuators B* 52, 169-178 (1998).

* cited by examiner

DEVICE AND METHOD FOR DETECTING SULFUR DIOXIDE AT HIGH TEMPERATURES

CROSS REFERENCE TO RELATED APPLICATION

This application is claiming benefit from U.S. Provisional Application No. 60/914,772 filed on Apr. 30, 2007.

This invention was made with government support under Contract Number DE-AC05-00OR22725 between the United States Department of Energy and UT-Battelle, LLC. The U.S. government has certain rights in this invention.

FIELD OF THE INVENTION

The present invention relates to methods and devices for detecting sulfur dioxide ($SO_2$), and more specifically, detecting $SO_2$ at high temperatures of at least 500° C.

BACKGROUND OF THE INVENTION

Sulfur dioxide ($SO_2$) is an unwanted by-product of many combustion processes. $SO_2$ is harmful to the environment as it produces acid rain when mixed with the water and oxygen present in the earth's atmosphere. Some of the most widespread sources of $SO_2$ include emissions from diesel engines and electrical power plants run by fossil fuels. Accordingly, there is increasing pressure to regulate and control the levels of $SO_2$ emanating from such sources, therefore monitoring of $SO_2$ levels is required.

All of the commonly-used devices for detecting $SO_2$ are limited to operating at maximum temperatures no more than about 40° C. An example of such a detector is the SO2-AF sensor from Alphasense Ltd. This sensor requires operation within the temperature range of −30 to 40° C. Other types of detectors used in the art include, for example, the electrolytic conductivity detector, mass spectrometer, and gas chromatography detector. Other popular detection methods are based on, for example, thermal conductivity and flame ionization. All of these detection methods are designed to operate more preferably at or near room temperature.

This upper limit on the operating temperature necessitates cooling of the combustion exhaust before measurement of the $SO_2$ level can take place. Cooling of the sample, and typically other pretreatment steps (such as scrubbing of hydrocarbons), can alter the sample by, for example, contamination, dilution or loss of sample species, or conversion of the $SO_2$ into sulfur trioxide ($SO_3$). In addition, the time required before the sample can be measured increases the chances that active species can decompose or react with other species. Furthermore, cooling of the sample causes condensation. The condensation is problematic because it interferes with the measurement process.

In addition to the difficulties caused by cooling, some of the devices currently used to measure $SO_2$ are not real-time in nature. For example, the electrolytic conductivity detector requires a gas sample to be absorbed by a Liquid electrolyte. These detectors operate by measuring the difference in electrical conductivity of the electrolyte material before and after the gas sample is absorbed by the electrolyte. The difference in electrical conductivity of the electrolyte indicates the type and/or concentration of the gas. See, for example, U.S. Pat. No. 4,440,726.

The absorption step required by the electrolytic conductivity detector has the disadvantage of increasing the measurement time. The long sample preparation time is particularly problematic in situations where $SO_2$ is needed to be monitored over time, continuously or in intervals. In such cases, extrapolation of a result back in time is required. The extrapolation can contribute to inaccuracy of the results as well as to an uncertainty of when a certain $SO_2$ level occurred.

There remains a need in the art for a simple and accurate method for directly measuring the level of $SO_2$ emanating from a combustion source. To improve the accuracy and usefulness of the measurement, there remains a particular need for a method that can determine in a real-time fashion the levels of $SO_2$ at the high temperatures encountered near combustion events.

SUMMARY OF THE INVENTION

These and other objectives, as will be apparent to those having ordinary skill in the art, have been achieved by providing an improved method and device for detecting sulfur dioxide ($SO_2$) in situ at the high temperatures often associated with combustion exhausts. The method involves contacting a $SO_2$-containing gaseous sample with the $SO_2$-detecting device of the invention, detecting a change in the electrical conductance (or electrical resistance) of the device as a result of contacting the device with an $SO_2$-containing sample, and correlating this change in conductance to the presence of or an amount of $SO_2$.

More specifically, the electrode device detects the presence of $SO_2$ by employing an arrangement of at least three electrically conductive electrodes on an oxygen ion-conducting substrate. This arrangement is preferably held at high temperature, normally between 500° C. and 800° C., and an electrical current (of fixed magnitude and temporal variation) is maintained between two electrodes while a specified electrical property related to or indicative of the conductance of the device is measured and monitored using a third electrode in electrical communication with one of the first two electrodes. $SO_2$ is detected based on the measured change in the specified electrical property. The specified electrical property is preferably voltage.

A fixed current ($I_o$) of specified magnitude and temporal variation is passed through two of the electrodes of the device before the device is contacted with the $SO_2$-containing sample. In a specific embodiment, before contact of the device with the $SO_2$-containing sample, a first measurement of the specified electrical property (e.g., voltage) is taken between the third electrode and one of the two electrodes engaged in the flow of the current $I_o$. This first measurement will be referred to as the "baseline" or "baseline reading."

The electrical conductance of the device changes when the device is contacted with the $SO_2$-containing sample. Accordingly, without a means for maintaining a constant current, the magnitude of the current between the first two electrodes would increase or decrease depending on the manner in which the electrical conductance of the device changes. However, in the method, the current is maintained (e.g., by use of a current-regulating device) even though conductance of the device has changed. During contact of the device with the $SO_2$-containing sample, and while the magnitude and any temporal variation of the current is being maintained between the first two electrodes, a second measurement of the specified electrical property is taken by the electronic measuring device, once again, between the third electrode and one of the two electrodes engaged in the fixed current flow $I_o$.

Sulfur dioxide is detected if a change in electrical conductance of the device is observed. In one embodiment, the change in electrical conductance is observed by observing a difference in the baseline and second measurement of a specified electrical property, as described above. The difference in the readings can also be used to infer the quantity of $SO_2$ that is present in the $SO_2$-containing sample.

The invention advantageously provides a method by which $SO_2$ can be quickly and easily measured in high-temperature emissions from a combustion source. Sulfur dioxide can be advantageously detected with a high degree of sensitivity, and the amount of $SO_2$ can be measured with a high level of accuracy. This method advantageously circumvents the need to cool the $SO_2$-containing gas before measuring the amount of $SO_2$. The method described herein is also advantageously less susceptible to deterioration of precision after repeated sample measurements (often referred to as "drift"). In addition, the invention can measure $SO_2$ selectively with minimal interference from other gases often found in combustion exhausts.

BRIEF DESCRIPTION OF THE DRAWINGS

FIG. 1A depiction of a preferred embodiment for a three-electrode sulfur dioxide ($SO_2$)-detecting device of the invention.

DETAILED DESCRIPTION OF THE INVENTION

The present invention is directed to a method and device for the selective detection of gaseous sulfur dioxide ($SO_2$) in high temperature gas samples. The gas samples primarily contemplated herein include those that emanate from combustion processes. The combustion processes are particularly those involving diesel fuels and coal of various grades. The temperatures of such emissions are typically at least 500° C., more typically at least 700° C., and even more typically at least 750 or 800° C. The device contemplated herein is capable of selectively detecting and/or measuring $SO_2$ at any of these temperatures.

The device detects the presence of $SO_2$ by employing an arrangement of at least three thermally stable, electrically conductive electrodes on a thermally stable, oxygen ion-conducting substrate wherein a fixed electrical current is maintained between two electrodes while an electrical property related to or indicative of the conductance of the device is measured and monitored using a third electrode in electrical communication with one of the first two electrodes. $SO_2$ is detected based on the measured change in electrical conductance.

The device is constructed of an oxygen ion-conducting substrate having on its surface at least three electrodes, hereinafter referred to as the first, second, and third electrodes.

The oxygen ion-conducting substrate can be constructed of any solid refractory oxygen ion-conducting material known in the art. The oxygen-ion conductivity of the substrate should be sufficient to establish electrical communication between the electrodes residing on its surface. Preferably, the oxygen ion-conducting substrate is composed of a yttria-stabilized zirconia (YSZ), such as those according to the general formula $Zr_{1-x}Y_xO_{2-x}$, where x is typically within the range 0.04-0.2. A particularly well-known YSZ material is according to the formula $Zr_{0.84}Y_{0.08}O_{1.92}$.

Other suitable oxygen-ion conducting substrate materials include, but are not limited to $M'_xZr_{1-x}O_{2-\delta}$, and $M'_xCe_{1-x}O_{2-\delta}$, where M' represents an element, that when present in the parent oxide, imparts oxygen ion conduction. Some examples of such elements include scandium (Sc) and gadolinium (Gd). Also suitable are the perovskite oxygen ion conductors, such as those according to the formula $La_{1-y}M''_yGa_{1-z}M'''_zO_{3-\delta}$, where M'' and M''' are metal ions, such as strontium (Sr) and gallium (Ga), that are incorporated to enhance oxygen ion conduction and/or stabilize the perovskite crystal structure.

Some other subclasses of suitable oxygen-ion conducting substrate materials include $Y_{1-a}Zr_aO_{2-\delta}$, $Sc_{1-a}Zr_aO_{2-\delta}$, $Ca_{1-a}Zr_aO_{2-\delta}$, $Mg_{1-a}Zr_aO_{2-\delta}$, $Gd_{1-b}Ce_bO_{2-\delta}$, $La_{1-b}Ce_bO_{2-\delta}$, $Yb_{1-b}Ce_bO_{2-\delta}$, $La_{2-b}Sr_bMo_2O_9$, $La_{2-b}Ba_bMo_2O_9$, $La_{1-b}Sr_bGa_{1-c}Mg_cO_{3-\delta}$, $La_{1-b}SrbGa_{1-a-d}Mg_dNi_dO_{3-\delta}$, $La_{1-b}Sr_bGa_{1-a-d}Mg_a$-$Co_dO_{3-\delta}$, $La_{1-b}Sr_bGa_{1-a-d}Mg_aFe_dO_{3-\delta}$, $La_2Mo_{2-e}Nb_eO_9$, $La_2Mo_{2-e}Ta_eO_9$, and $La_2Mo_{2-e}W_eO_9$, where $0<a<0.2$, $0<b<0.3$, $0<c<0.3$, $a+d<0.3$, $0<e<1$, and $\delta$ represents an incremental variable of about 0 to about 0.05.

A suitable oxygen-ion conducting substrate is preferably produced by tape-casting and sintering commercially obtained YSZ. Other methods of production include, for example, roll compaction, injection molding, and the like, followed by appropriate heat or other treatments to remove processing aids and densify the substrate. The substrate can be of any suitable thickness, but is more typically in the range of about 0.05 cm to about 0.3 cm.

The electrode materials are electrically conductive (typically, with an electronic conductivity ($\sigma_e$)> about 0.01 S/cm at 500° C.) materials that are stable and refractory in air at temperatures of at least 500° C. By stable or refractory is meant that the materials are resistant to chemical and microstructural changes at the temperatures and oxygen partial pressures normally encountered in combustion exhausts. An example of chemical instability would be significant uptake of oxygen and an example of a microstructural instability would be a tendency to spall from the substrate. One class of materials fulfilling the above stability requirements are the electrically conductive oxides used as electrodes and interconnects in solid oxide fuel cells. These include material compositions having, for example, the perovskite crystal structure and the formula:

$$Ln_{1-y}A_yM_{1-z}M'_zO_{3-\delta} \quad (1)$$

In formula (1), Ln represents a lanthanide or scandium-group metal. The lanthanide metal can be any of the elements in the Periodic Table of the Elements having an atomic number of 57 to 71. The lanthanide metal is more typically lanthanum (La). The symbol A represents an alkaline earth metal. The alkaline earth metal can be any of the metals from Group IIA of the Periodic Table, and more typically, magnesium (Mg), calcium (Ca), strontium (Sr), or barium (Ba). The symbol M represents a first row transition metal, Suitable first row transition metals can include, for example, scandium (Sc), titanium (Ti), vanadium (V), chromium (Cr), manganese (Mn), iron (Fe), cobalt (Co), nickel (Ni), copper (Cu), and zinc (Zn). More typically, the transition metal is Cr, Mn, Fe, Co, Ni, or Cu. The symbol M' represents either a first row transition metal or an alkaline earth metal, both as described above. The subscripts y and z can both be, independently, any suitable value equal to or greater than 0 and equal to or less than 1. More preferably, $0 \leq y \leq 0.4$ and $0 \leq z \leq 1$. The symbol $\delta$ is as already defined.

One subclass of formula (1) results when y is zero. When y is zero, formula (1) is simplified to:

$$LnM_{1-z}M'_zO_{3-\delta} \qquad (2)$$

A more preferred subclass of formula (2) is given by the formula:

$$LaM_{1-z}M'_zO_{3-\delta} \qquad (3)$$

Another preferred subclass of formula (2) is given by the formula:

$$LnCr_{1-z}M'_zO_{3-\delta} \qquad (4)$$

An even more preferred subclass of formula (2) is given by the formula:

$$LaCr_{1-z}M'_zO_{3-\delta} \qquad (5)$$

In formulas (2), (3), (4), and (5), Ln, M, Mt, z, and $\delta$ are as defined above for formula (1). In a preferred embodiment, M' in any of formulas (2), (3), (4), or (5) is an alkaline earth metal. More preferably, the alkaline earth metal is magnesium. Accordingly, an even more preferred composition for the electrode materials is given by the formula:

$$LaCr_{1-z}Mg_zO_{3-\delta} \qquad (6)$$

A preferred composition within formula (6) is $LaCr_{0.85}Mg_{0.15}O_{3-\delta}$.

Another subclass of formula (1) results when z is zero. When z is zero, formula (1) is simplified to:

$$Ln_{1-y}A_yMO_{3-\delta} \qquad (7)$$

A more preferred subclass of formula (7) is according to the formula:

$$La_{1-y}A_yMO_{3-\delta} \qquad (8)$$

Another preferred subclass of formula (7) is according to the formula:

$$Ln_{1-y}Sr_yMO_{3-\delta} \qquad (9)$$

More preferably, in formula (9) above, Ln represents lanthanum (La), samarium (Sm), or yttrium (Y). A preferred composition when Ln=Sm is $Sm_{0.6}Sr_{0.4}CoO_{3-\delta}$.

An even more preferred subclass of formula (7) is according to the formula:

$$La_{1-y}Sr_yMO_{3-\delta} \qquad (10)$$

More preferably, M represents Mn, Fe, Cr, or Co for any of the formulas (7)-(10) shown above. Even more preferred compositions are according to formula (10) where M is either Mn, Fe, Cr, or Co, as shown in the following formulas:

$$La_{1-y}Sr_yMnO_{3-\delta} \qquad (11)$$

$$La_{1-y}Sr_yFeO_{3-\delta} \qquad (12)$$

$$La_{1-y}Sr_yCrO_{3-\delta} \qquad (13)$$

$$La_{1-y}Sr_yCoO_{3-\delta} \qquad (14)$$

A particularly preferred composition according to formula (11) is $La_{0.8}Sr_{0.2}MnO_{3-\delta}$. Other suitable compositions include $La_{0.9}Sr_{0.1}MnO_{3-\delta}$ and $La_{0.7}Sr_{0.3}MnO_{3-\delta}$. A particularly preferred composition according to formula (12) is $La_{0.8}Sr_{0.2}FeO_{3-\delta}$. Other suitable compositions include $La_{0.9}Sr_{0.1}FeO_{3-\delta}$ and $La_{0.7}Sr_{0.3}FeO_{3-\delta}$. A particularly preferred composition according to formula (13) is $La_{0.75}Sr_{0.25}CrO_{3-\delta}$. A particularly preferred composition according to formula (14) is $La_{0.8}Sr_{0.2}CoO_{3-\delta}$.

Another subclass of formula (1) results when both y and z are not zero. When this is the case, a more preferred subclass of formula (1) is according to the formula:

$$La_{1-y}A_yM_{1-z}M'_zO_{3-\delta} \qquad (15)$$

Another preferred subclass of formula (1) is according to the formula:

$$Ln_{1-y}Sr_yM_{1-z}M'_zO_{3-\delta} \qquad (16)$$

An even more preferred subclass of formula (1) is according to the formula:

$$La_{1-y}Sr_yM_{1-z}M'_zO_{3-\delta} \qquad (17)$$

In a preferred embodiment, M and M' in any of formulas (1), (15), (16), and (17) are both first row transition metals. More preferably, M and M' represent different metals selected from Co, Fe, Mn, and Cr. Some subclasses of formula (17) include:

$$La_{1-y}Sr_yCo_{1-z}Fe_zO_{3-\delta} \qquad (18)$$

$$La_{1-y}Sr_yMn_{1-z}Cr_zO_{3-\delta} \qquad (19)$$

$$La_{1-y}Sr_yMn_{1-z}Fe_zO_{3-\delta} \qquad (20)$$

$$La_{1-y}Sr_yFe_{1-z}Cr_zO_{3-\delta} \qquad (21)$$

$$La_{1-y}Sr_yCo_{1-z}Mn_zO_{3-\delta} \qquad (22)$$

$$La_{1-y}Sr_yCo_{1-z}Cr_zO_{3-\delta} \qquad (23)$$

A particularly preferred composition according to formula (18) is $La_{0.6}Sr_{0.4}Co_{0.2}Fe_{0.8}O_{3-\delta}$. Another suitable composition according to formula (18) is $La_{0.6}Sr_{0.4}Co_{0.8}Fe_{0.2}O_{3-\delta}$. A particularly preferred composition according to formula (19) is $La_{0.75}Sr_{0.25}Mn_{0.5}Cr_{0.5}O_{3-\delta}$.

Another subclass of formula (1) results when both y and z are zero. These compositions are according to the formula:

$$LnMO_{3-\delta} \qquad (24)$$

A preferred example of a composition according to formula (24) is lanthanum chromium oxide, $LaCrO_3$.

Another suitable class of conductive oxide compositions for the electrodes include the oxides according to the formula:

$$M'M''O_3 \qquad (25)$$

In formula (25), M' and M" are typically different metal cations. The metal cations can be independently selected from, for example, the first, second, and third row transition metals, lanthanide metals, and main group (particularly Groups IIIA and IVA) metals, such as Pb and Bi. More typically, M' represents a trivalent metal (often from Group IIIB) and M" represents a transition metal (more preferably a first row transition metal). Some examples of such oxides include $LaCrO_3$, $LaMnO_3$, $LaFeO_3$, $YCrO_3$, and $YMnO_3$, all having the perovskite structure.

It is also possible for M' and M" in formula (25) to be the same metal, wherein formula (25) reduces to $M'_2O_3$. In these compositions, M' is preferably a first row transition metal. Some examples of such compositions include $Cr_2O_3$, and $Fe_2O_3$, both having the corundum crystal structure, and $Mn_2O_3$, having the bixbyite crystal structure.

Another suitable class of conductive oxide compositions for the electrode materials include the spinel crystal structure oxides having the chemical formula $$M'M''_2O_4 \quad (26)$$

In formula (26), M' and M'' are metal cations. Typically, M'' is a trivalent metal ion and M' is a divalent metal ion. More typically, M' and M'' independently represent transition metals, and more typically, first row transition metals. Some examples of suitable spinel crystal structure compositions include $NiCr_2O_4$, $CuCr_2O_4$, $ZnCr_2O_4$, $CdCr_2O_4$, $MnCr_2O_4$, $NiMn_2O_4$, $CuMn_2O_4$, $ZnMn_2O_4$, $CdMn_2O_4$, $NiCo_2O_4$, $CuCo_2O_4$, $ZnCo_2O_4$, $CdCo_2O_4$, $MnCo_2O_4$, $NiFe_2O_4$, $CuFe_2O_4$, $ZnFe_2O_4$, $CdFe_2O_4$, and $MnFe_2O_4$. M' and M'' can also be combinations of metals, such as in $(Co,Zn)Cr_2O_4$, and $Ni(Cr, Fe)_2O_4$.

Other suitable conductive oxide compositions for the electrode materials include those of the general formula:

$$Ln_{2-y}A_yMO_4 \quad (27)$$

In formula (27), Ln, A, and y are as defined above. Preferably, Ln represents La, Sm, or Ce. More preferably, Ln represents La, as in the following formula:

$$La_{2-y}A_yMO_4 \quad (28)$$

Preferably, A represents Mg, Ca, Sr, or Ba, and more preferably Sr, as in the following formula:

$$Ln_{2-y}Sr_yMO_4 \quad (29)$$

Even more preferably, On is La and A is Sr in formula (27). These compositions are according to the formula:

$$La_{2-y}Sr_yMO_4 \quad (30)$$

More preferably, M in any of the formulas (27)-(30) represents Co or Ni. Even more preferred compositions are according to formula (30) when M is Co or Ni, as shown in the following formulas:

$$La_{2-y}Sr_yCoO_4 \quad (31)$$

$$La_{2-y}Sr_yNiO_4 \quad (32)$$

An example of a preferred composition according to formula (31) is $La_{1.8}Sr_{0.2}CoO_4$. An example of a preferred composition according to formula (32) is $La_{1.8}Sr_{0.2}NiO_4$.

Other suitable conductive oxide compositions for the electrode materials include, for example, $La_2CoNiO_5$, as well as the class of modified cerias, such as those according to the general formula:

$$Ce_{1-y}Ln'_yO_{2-\delta} \quad (33)$$

In formula (33), Ln' includes the lanthanides, as described above, as well as the early transition metals, particularly those of Group IIIB (scandium group), Group IVB (titanium group), and Group V (vanadium group). Some examples of suitable doped ceria compositions include $Ce_{0.8}Sm_{0.2}O_{2-\delta}$, $Ce_{0.8}Sm_{0.2}O_{2-\delta}$, $Ce_{0.8}La_{0.2}O_{2-\delta}$, and $Ce_{0.8}Y_{0.2}O_{2-\delta}$. The composition can also be unmodified ceria (i.e., $CeO_2$).

The electrodes may also be constructed of a noble metal or noble metal alloy. Noble metals are those known to be resistant to corrosion or oxidation, in contrast to most other metals. They are typically expensive on a weight basis in comparison with other metals. Some examples of suitable noble metals include platinum (Pt), palladium (Pd), gold (Au), silver (Ag), rhodium (Rh), and iridium (Ir). The noble metal alloys can be binary, ternary, or higher alloys. Some examples of noble metal alloys containing only noble metals include Pt—Rh, Pt—Ir, Pt—Pd, Pt—Ag, Pt—Au, Ag—Pd, and Au—Pd.

The noble metal alloy can also include one or more non-noble metals. Preferably, the molar percentage of non-noble metals in the alloy is no more than about 10%. The non-noble metal is typically selected from Co, Ni, and Cu. Some examples of these types of noble metal alloys include Au—Co, Au—Ni, Pt—Ni, Pt—Co, Pt—Cu, and Co—Cr—Pt.

In a preferred embodiment, the first and second electrodes are both constructed of conductive oxide compositions, while the third electrode is a noble metal or noble metal alloy. While the first and second electrodes are both conductive oxides, their compositions are independent. Accordingly, the first and second electrodes can have the same or different conductive oxide composition.

In a first embodiment, the first and second electrodes are independently constructed of compositions within formula (1), $Ln_{1-y}A_yM_{1-z}M'_zO_{3-\delta}$.

In a second embodiment, the first and second electrodes are independently constructed of compositions within formula (2), $LnM_{1-z}M'_zO_{3-\delta}$.

In a third embodiment, the first and second electrodes are independently constructed of compositions within formula (3), $LaM_{1-z}M'_zO_{3-\delta}$.

In a fourth embodiment, the first and second electrodes are independently constructed of compositions within formula (4), $LnCr_{1-z}M'_zO_{3-\delta}$.

In a fifth embodiment, the first and second electrodes are independently constructed of compositions within formula (5), $LaCr_{1-z}M'_zO_{3-\delta}$.

In each of the first-fifth embodiments given above, it is more preferable that M' represents an alkaline earth metal. The alkaline earth metal is more preferably Mg.

In a sixth embodiment, the first and second electrodes are independently constructed of compositions within formula (6), $LaCr_{1-z}Mg_zO_{3-\delta}$.

In one case, the first and second electrodes are of different compositions selected from any of the formulas 1-6. For example, the first electrode can be of the composition $LaCr_{0.85}Mg_{0.15}O_{3-\delta}$ while the second electrode is of the composition $LaCr_{0.85}Sr_{0.15}O_{3-\delta}$. In another case, the first and second electrodes are of the same composition within any of the formulas 1-6. For example, the first and second electrodes can both be of the composition $LaCr_{0.85}Mg_{0.15}O_{3-\delta}$ or $LaCr_{0.85}Sr_{0.15}O_{3-\delta}$.

In a seventh embodiment, the first and second electrodes are independently constructed of compositions within formula (7), $Ln_{1-y}A_yMO_{3-\delta}$.

In an eighth embodiment, the first and second electrodes are independently constructed of compositions within formula (8), $La_{1-y}A_yMO_{3-\delta}$.

In a ninth embodiment, the first and second electrodes are independently constructed of compositions within formula (9), $Ln_{1-y}Sr_yMO_{3-\delta}$.

In a tenth embodiment, the first and second electrodes are independently constructed of compositions within formula (10), $La_{1-y}Sr_yMO_{3-\delta}$.

In each of the sixth-tenth embodiments given above, it is more preferable that M represents Mn, Fe, Cr, or Co, as shown above by the formulas (11)-(14). In one case, the first and second electrodes are of different compositions selected from any of the formulas 7-14. For example, the first electrode can be of the composition $La_{0.8}Sr_{0.2}MnO_{3-\delta}$ while the second electrode is of the composition $La_{0.8}Sr_{0.2}FeO_{3-\delta}$. In another case, the first and second electrodes are of the same composition within any of the formulas 7-14. For example, the first and second electrodes can both be of the composition $La_{0.8}Sr_{0.2}MnO_{3-\delta}$, $La_{0.8}Sr_{0.2}FeO_{3-\delta}$, $La_{0.8}Sr_{0.2}CrO_{3-\delta}$, or $La_{0.8}Sr_{0.2}CoO_{3-\delta}$.

In an eleventh embodiment, the first and second electrodes are independently constructed of compositions within formula (15), $La_{1-y}A_yM_{1-z}M'_zO_{3-\delta}$.

In a twelfth embodiment, the first and second electrodes are independently constructed of compositions within formula (16), $Ln_{1-y}Sr_yM_{1-z}M'_zO_{3-\delta}$.

In a thirteenth embodiment, the first and second electrodes are independently constructed of compositions within formula (17), $La_{1-y}Sr_yM_{1-z}M'_zO_{3-\delta}$.

In each of the eleventh-thirteenth embodiments, M and M' are preferably both first row transition metals. More preferably, M and M' represent different metals selected from Co, Fe, Mn, and Cr, as shown above by the formulas (18)-(23). In one case, the first and second electrodes are of different compositions selected from any of the formulas (15)-(23). For example, the first electrode can be of the composition $La_{0.6}Sr_{0.4}Co_{0.2}Fe_{0.8}O_{3-\delta}$ while the second electrode is of the composition $La_{0.6}Sr_{0.4}Co_{0.8}Fe_{0.2}O_{3-\delta}$. In another case, the first and second electrodes are of the same composition within any of the formulas (15)-(23). For example, the first and second electrodes can both be of the composition $La_{0.6}Sr_{0.4}Co_{0.2}Fe_{0.8}O_{3-\delta}$ or $La_{0.6}Sr_{0.4}Co_{0.8}Fe_{0.2}O_{3-\delta}$.

In a fourteenth embodiment, the first and second electrodes are independently constructed of compositions within formula (24), $LnMO_{3-\delta}$.

In a fifteenth embodiment, the first and second electrodes are independently constructed of compositions within formula (25), $M'M''O_3$.

In a sixteenth embodiment, the first and second electrodes are independently constructed of compositions within formula (26), $M'M''_2O_4$.

In a seventeenth embodiment, the first and second electrodes are independently constructed of compositions within formula (27), $Ln_{2-y}A_yMO_4$.

In a eighteenth embodiment, the first and second electrodes are independently constructed of compositions within formula (28), $La_{2-y}A_yMO_4$.

In a nineteenth embodiment, the first and second electrodes are independently constructed of compositions within formula (29), $Ln_{2-y}Sr_yMO_4$.

In a twentieth embodiment, the first and second electrodes are independently constructed of compositions within formula (30), $La_{2-y}Sr_yMO_4$.

In each of the seventeenth-twentieth embodiments, M is preferably Co or Ni.

In a twenty-first embodiment, the first and second electrodes are independently constructed of compositions selected from formulas (31) and (32), $La_{2-y}Sr_yCoO_4$ and $La_{2-y}Sr_yNiO_4$, respectively.

In a twenty-second embodiment, the first and second electrodes are independently constructed of compositions selected from formula (33), $Ce_{1-y}Ln'_yO_{2-\delta}$.

In another embodiment, the first electrode is constructed of a composition according to a formula selected from formulas 1-33, while the second electrode is constructed of a different composition according to a different formula selected from formulas 1-33. For example, the first electrode can be constructed of a composition according to any of formulas 15-23, while the second electrode can be constructed of a composition according to any of formulas 2-6. Even more particularly, the first electrode can be constructed of a composition having the formula $La_{0.6}Sr_{0.4}Co_{0.2}Fe_{0.8}O_{3-\delta}$, while the second electrode can be constructed of a composition having the formula $LaCr_{0.85}Mg_{0.15}O_{3-\delta}$. Another example is the first electrode having a composition $La_{0.6}Sr_{0.4}Co_{0.2}Fe_{0.8}O_{3-\delta}$ and the second electrode having the composition $La_{0.8}Sr_{0.2}MnO_{3-\delta}$. Another example is the first electrode having a composition $La_{0.6}Sr_{0.4}Co_{0.2}Fe_{0.8}O_{3-\delta}$ and the second electrode having the composition $La_{0.8}Sr_{0.2}FeO_{3-\delta}$. Yet another example is the first electrode having a composition $LaCr_{0.85}Mg_{0.15}O_{3-\delta}$ and the second electrode having the composition $La_{0.8}Sr_{0.2}MnO_{3-\delta}$ or $La_{0.8}Sr_{0.2}FeO_{3-\delta}$.

In another embodiment, all three electrodes are constructed of any of the conductive oxide compositions described above.

In another embodiment, one of the electrodes is constructed of a conductive oxide material while the other two electrodes are independently constructed of any of the noble metal or alloy compositions described above. By having independent constructions, the noble metal electrodes can have the same or different noble metal or alloy compositions. For example, the first or second electrode can be constructed of gold or a gold alloy and the third electrode constructed of platinum or a platinum alloy. Another example is the first or second electrode constructed of platinum and the third electrode constructed of a platinum alloy, such as platinum-nickel. Yet another example is two of the electrodes being constructed of platinum. Alternatively, the first and second electrodes can be independently constructed of a noble metal or alloy composition while the third electrode is constructed of a conductive oxide.

In yet another embodiment, all three of the electrodes are independently constructed of any of the noble metal or alloy compositions described above.

In one embodiment, one or more of the electrodes are constructed entirely of any one of the materials described above. In another embodiment, one or more of the electrodes are constructed partially of any one of the materials described above. For example, the electrodes can be partially constructed of any of the materials described, and in addition, include an overlayer, underlayer, interlayer, an encasing, or other features constructed of any other suitable material that permits detection or measurement of $SO_2$ at temperatures of at least 500° C.

The electrodes can be deposited onto the substrate using any of the well-known deposition methods known in the art. Some examples of suitable methods include sputtering, chemical and physical vapor deposition, spin coating of sol-gel solutions, and pulsed laser deposition of a dispersion of electrode material followed by appropriate thermal treatment. Dispersions for screen printing can be made using commercially available powders and processing aids. Alternatively, dispersions may be obtained commercially in a form suitable for screen printing.

The electrodes can be of any suitable thickness. Preferably, the thickness of the electrodes is, independently, in the range of about 1 micron to about 500 microns. More preferably, the thickness is in the range of about 5 microns to about 100 microns, and even more preferably, about 20 to about 50 microns. The individual thicknesses of the electrodes are independent, and thus, can all be the same or can vary. It may be advantageous in one embodiment for the thicknesses of all electrodes to about the same (e.g., with no more than about 1% variation in thickness), whereas in another embodiment it may be advantageous for at least one electrode to vary in thickness (e.g., within 1-10%, or above 10%).

If desired, the device can include more than three electrodes, such as four, five, six, or any number of electrodes. For example, it may be desired to include a fourth electrode constructed of a noble metal or conductive oxide material. The additional electrodes can serve any of a variety of purposes. For example, it may be desirable to include an additional pair of electrodes capable of measuring the abundance of another species of interest (e.g., $O_2$ or $H_2O$) or to correct for aging of the device during use. It may also be desired to position one or more electrodes such that they are isolated from the gas being sensed, thereby permitting additional inferences (for example, the $O_2$ concentration) to be made about the gas being sensed. Preferably, to serve one of the aforementioned purposes, the additional electrodes are not sensitive to the presence of $SO_2$.

A multiple number of electrodes may also be provided in the form of an array of electrodes. The array can be, for example, linearly segmented or dotted. The individual electrodes in an array, or portion of an array, may serve the same or different functions.

The electrodes can be located on the same face or plane of the substrate (i.e., coplanar). Alternatively, the electrodes can be located on different faces or planes of the substrate.

The electrodes can have any desired shape. For example, each electrode can independently be circular, a circular sector (e.g., semi-circular, quarter-circular), a circular segment, crescent, oval, triangular, quadrilateral (e.g., square, rectangular), pentagonal, or hexagonal. In addition, the electrodes can possess any desired pattern or more unusual or irregular shape. For example, they can be arranged to be interdigitated, ruled, coiled, spiraled, dumbbell, or horseshoe.

The electrodes are separated by a suitable space. For electrodes having adjacent, colinearly-disposed (i.e., parallel) straight edges, there can be a single, essentially unvaried spacing between the electrodes. The spacing can be varied by, for example, changing the angle of one electrode with respect to the other. The spacing can also vary when at least one of the electrodes does not contain a straight edge, or contains a straight edge that is not parallel to another straight edge. There can also be more than one spacing, such as in the case where electrode segments from different electrodes are interdigitating or interpenetrating with each other. The spacing between electrodes is preferably about 0.1 cm but may be as small as about 0.01 cm or up to about 10 cm In the method for detecting $SO_2$, an electrical current (I), i.e., a starting or fixed current, of specified i) maximum magnitude and ii) temporal variation is driven between the first and second electrodes before the device is contacted with the $SO_2$-containing sample. The temporal variation can be zero, in which case the current is direct current (DC), or the temporal variation can be one of the various simple periodic types known in the art, for example sinusoidal, "sawtooth", or "squarewave", or a more complex periodic variation. When the current is DC, the algebraic sign and magnitude must be specified. When the current is periodically varying in time, typically the dependence of the current on time for one complete period of the variation must be specified.

The starting current is driven by any means known in the art, such as by a current-regulating device in simultaneous electrical communication with (i.e., bridging) the first and second electrodes. The current-regulating device can be, for example, any of the voltage-applying devices known in the art for inducing an electrical current flow between electrically conductive electrodes. The current-regulating device can be a permanent part of the device, or separately attachable. The voltage necessary for inducing a starting current between the first and second electrodes can be readily determined based on such factors as the chemical and physical construction of the electrodes, choice of substrate, arrangement of electrodes, and so on. Typically, a steady state (in the case of DC electrical currents) or root mean square (in the case of time-varying currents) voltage of from at least about 10 mV and up to about 10V is capable of providing a starting DC or root mean square current of at least about 0.01 mA and up to about 10 mA.

In a preferred embodiment, the device is preheated before contacting the device with the $SO_2$-containing sample. The device is preferably preheated to a temperature capable of preventing condensation of vapors on the electrodes when the device is contacted with the $SO_2$-containing sample. In addition, since the electrical conductivity of the electrodes and electrolyte often increase with temperature, the preheating step can serve the additional purpose of imparting an acceptable level of conductivity to the electrodes. Typically, the device is preheated to a temperature of at least 500° C. Preferably, the device is heated to a temperature of at least the temperature of the $SO_2$-containing gas being sensed, and more preferably, to at least 10° C., 20° C., 30° C., 40° C., 50° C., or 100° C. above the gas temperature. Generally, the $SO_2$ source temperature needs to be known in order to adjust the temperature of the device accordingly. Any of the methods known in the art for estimating or measuring the temperature of the $SO_2$ source can be used herein for that purpose.

The preheating step can be initiated either before, during, or after the current flow has been established between the first and second electrodes, but before contact of the device with the $SO_2$-containing sample. Heating of the device can be accomplished in any of a variety of ways, including any of the methods commonly known in the art. For example, the device can be incorporated as the outer layer of a laminated structure, where the inner laminations comprise a refractory, electrically insulating material, such as aluminum oxide, encasing a resistive heating element, such as a noble metal. The refractory material being heated by the inner heating element is preferably in direct contact with the oxygen-ion conducting substrate of the device. Alternatively, it may also be desired to use a suitably sized heating element to partially surround the $SO_2$-detecting device.

Preferably, the device is allowed to reach thermal equilibrium. However, it is also contemplated that the device may include means for thermal cycling by which an original sensing state is restored.

Once the device has reached the desired operating temperature, before the device is contacted with the $SO_2$-containing sample, and while the current is flowing between the first and second electrodes, an electrical property is recorded (e.g., read or measured by the device or observed or recorded by the operator) between the first and third or the second and third electrodes by means of an electronic measuring device in electrical communication with the first and third or second and third electrodes. This observation is hereinafter referred to as the "first measurement," "baseline," "baseline reading," or "baseline measurement." The electrical property being measured and recorded by the operator or device is preferably voltage.

The electrical property can be measured by means of any suitable electronic measuring device known in the art capable of measuring the specified electrical property (e.g., voltage) between two electrodes. Preferably, when the property being measured is voltage, the device is a voltmeter with a very high input impedance (sometimes referred to as an electrometer).

When the device is contacted with $SO_2$, the electrical conductance of the device will change. Typically, on contact of the device with $SO_2$, the electrical conductance of the device decreases, i.e., the electrical resistance or impedance increases. However, the present invention also contemplates situations in which the electrical resistance may decrease. The method works in the same manner whether electrical resistance increases or decreases. In the absence of the current-regulating device in electrical communication with the first and second electrodes, the current flowing between the first and second electrodes would decrease or increase in response to an increase or decrease, respectively, in the electrical resistance. The current-regulating device functions to maintain a fixed current between the first and second electrodes while a change in resistance occurs in the device. The current-regulating device typically maintains the current by adjusting an applied voltage of appropriate magnitude. The magnitude of the voltage required for maintaining the current can be readily established either manually or automatically using methods known in the art.

While the device is in contact with the $SO_2$-containing sample, and while the current is being maintained between the first and second electrodes, the electrical property (i.e., voltage) is observed once again, by means of the electronic measuring device, between the first and third or the second and third electrodes. This observation is hereinafter referred to as the "second measurement" or "second reading."

The second measurement is compared to the baseline to observe or record any difference in the specified electrical property. This difference, which can be expressed in any convenient form, such as a percent change, is then used to deduce the presence of (i.e., detection) of $SO_2$ in the sample. The difference can also be indicative of the amount (i.e., a quantitative measurement) of $SO_2$ by correlating the magnitude of the change between the first and second readings with prior knowledge (i.e., a calibration) of how the presence of $SO_2$ affects the specified electrical property. As used herein, "detection" also includes quantifying the amount of $SO_2$.

Typically, the electrical property being measured is voltage. Aside from the presence of $SO_2$, the measured voltage between the first and third or second and third electrodes is typically dependent on several other factors, including the physical and chemical construction of the electrodes and substrate, the magnitude of the base current being applied, and the temperature of the device.

In a preferred embodiment, the magnitude of the measured voltage is automatically converted by a computational device to a value expressing an amount of $SO_2$. The conversion to an amount can be accomplished by any suitable equation or algorithm known in the art or found by experiment to provide an accurate numerical output of the amount of $SO_2$ from the measured voltage.

The amount of $SO_2$ detected can be expressed in any convenient form, such as parts per million (ppm), parts per billion (ppb), and the like. The measured voltage can also be converted by an auxiliary computational and/or converting device to a signal indicating the presence or absence of $SO_2$. Alternatively, the auxiliary device may use a desired signal or set of different signals to indicate the presence of $SO_2$ within specified ranges or beyond or below a certain threshold. The signal can be, for example, an indicator provided by a screen, a light, or a sound.

The device contemplated herein is generally suitable for detecting as little as 1 ppm of $SO_2$. Typical amounts of $SO_2$ in most samples are in the range of about 50 ppm to about 5000 ppm, and more typically, about 10 ppm to about 500 ppm.

The detection or measurement of $SO_2$ according to the method herein is preferably selective. By being selective, the device is capable of generating a much stronger electrical response to $SO_2$ than to other chemical species that may also be present. Some commonly encountered chemical species normally accompanying $SO_2$ in $SO_2$-containing samples include, for example, hydrocarbons (e.g., propylene ($C_3H_6$)), nitric oxide (NO), carbon monoxide (CO), carbon dioxide ($CO_2$), and ammonia ($NH_3$). The concentration of oxygen (i.e., [$O_2$]) may also vary.

Preferably, the response magnitude (e.g., of measured voltage) from the device for $SO_2$ is at least ten times the response magnitude for any other chemical species. For example, the device can typically exhibit at least a 50 mV output in the measured voltage for about 10 ppm of $SO_2$ while exhibiting a 5 mV output for the same concentration of any of the other chemical species. More preferably, the electrical response for any chemical species other than $SO_2$ is insignificant or virtually zero (e.g., 1-5 mV for 100 ppm of a chemical species other than $SO_2$).

Examples have been set forth below for the purpose of illustration and to describe the best mode of the invention at the present time. However, the scope of this invention is not to be in any way limited by the examples set forth herein.

Example 1

Operation of a Three-Electrode Device

Figure 1:
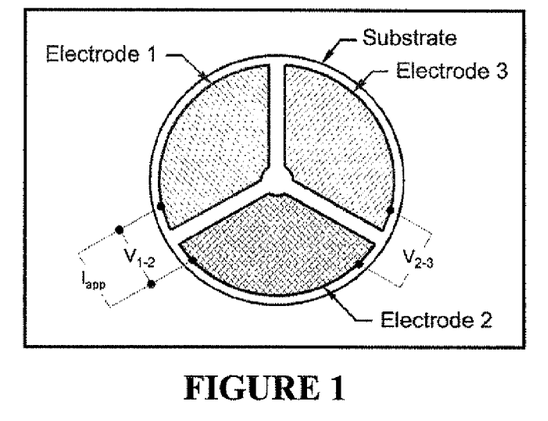

A preferred embodiment of the invention is shown in FIG. 1. As shown in FIG. 1, this embodiment includes three electrodes, roughly equal in area, on an oxygen ion-conducting substrate. The oxygen ion-conducting substrate has the composition $Zr_{0.84}Y_{0.08}O_{1.92}$. The composition of electrode 1 is $LaCr_{0.98}O_3$, the composition of electrode 2 is $LaCr_{0.85}Mg_{0.15}O_3$, and the composition of electrode 3 is Pt. The device shown in FIG. 1 was mounted in a fixture that allowed electrical contact (via Pt mesh) to each of the three electrodes and also allowed gas mixtures to be flown directly onto the electroded side of the device. The fixture and device were placed in a resistively heated tube furnace and heated to a temperature of 900° C. A gas mixing unit was then used to supply a mixture of 7 vol % $O_2$, 1.2 vol % $H_2O$ (balance $N_2$) to the device. A Keithley 2400 SourceMeter was then used to drive a DC current of 0.125 mA ($I_{app}$ in FIG. 1) from electrode 1 to electrode 2. This caused the DC voltages shown in FIG. 1 as "$V_{1-2}$" and "$V_{2-3}$" to be about 100 and 12 mV, respectively when measured with a Keithley 617 electrometer.

Figure 2:
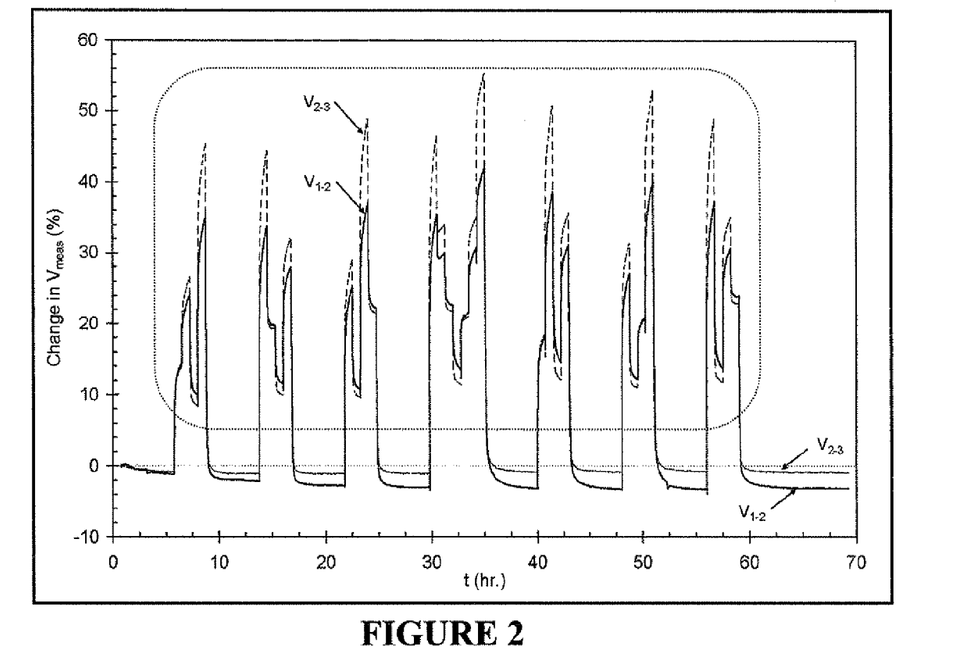
FIG. 2 Data showing the effect of $SO_2$ on measured voltage as a function of time. During the period of data collection delineated by the dotted rectangle, $SO_2$ is being supplied at a concentration of either 2, 5.5, 13, or 31 ppm. There is no $SO_2$ being supplied at other times. "$V_{1-2}$" and "$V_{2-3}$" are defined in FIG. 1. Measurements made at an operating temperature of 900° C., ambient gas concentration 7 vol% $O_2$, 1.2 vol% $H_2O$ (g) in $N_2$ balance gas.

The gas mixing unit was then programmed to add $SO_2$ at levels of 2, 5.5, 13, or 31 ppm to the gas mixtures at approximately 8 hour intervals. Each level of $SO_2$ was maintained for 45 minutes during these additions and the sequence of $SO_2$ levels was varied in random order during each addition. The $SO_2$ addition in the mixtures was zero at all other times. The measured values of "$V_{1-2}$" and "$V_{2-3}$" were recorded by a computer and then converted into percent changes from the steady state values observed for each at the beginning of the test. The resultant data are shown in FIG. 2. The presence of $SO_2$ causes (on a percent basis) large reversible changes in both $V_{1-2}$ (the voltage being used to drive the fixed 0.125 mA current from electrode 1 to electrode 2) and $V_{2-3}$ (the voltage being measured between electrode 2 and electrode 3).

The data shown in FIG. 2 demonstrate that though it is possible to detect $SO_2$ with a two-electrode device, there are several advantages in using three electrodes. For example, it is shown that in the three-electrode system the percent changes in $V_{2-3}$ caused by the presence of $SO_2$ are larger than the percent changes in $V_{1-2}$ caused by the presence of $SO_2$. The value of $V_{2-3}$ at the cessation of the measurements is also very close to its value at the initiation of the measurements, and thus, shows a low level of drift in the measured values. $V_{1-2}$, on the other hand, drifted downward by about 10% over the course of the measurements. Accordingly, the above results show that the three-electrode system is less susceptible to drift of the measurement.

Example 2

Effect of Sign and Magnitude of Applied Direct Current

A device having one electrode made of $La_{0.6}Sr_{0.4}Co_{0.2}Fe_{0.8}O_3$ (electrode 1), one electrode made of $LaCr_{0.85}Mg_{0.15}O_3$ (electrode 2), and one made of Pt (electrode 3) was constructed and operated in accordance with Example 1, except that the operating temperature was 750° C. and no $H_2O$ was intentionally added to the gas mixtures. The 2400 SourceMeter of Example 1 was programmed to apply DC currents of −0.2, −0.15, −0.1, −0.05, 0, 0.5, 0.125, 0.2, and 0 mA for periods of one hour each. The gas mixing unit was programmed to supply 25 ppm pulses of $SO_2$ to the device at each of these current settings. The pulses of $SO_2$ were eight minutes in duration and were applied at each current setting after the applied DC current had been constant for 26 minutes.

Figure 3:
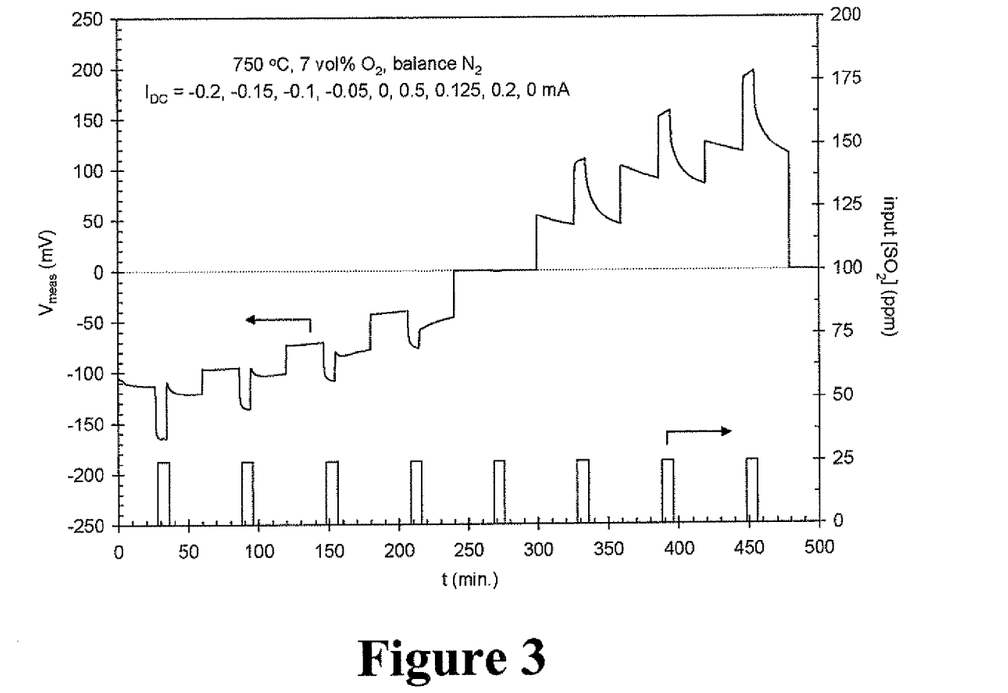
FIG. 3 Data showing how 25 ppm of $SO_2$ affect measured voltage ($V_{meas}$) at different levels of applied DC current. Operating temperature=750° C., ambient gas 7 vol % $O_2$, with $N_2$ comprising the balance.

The resultant measurements are shown in FIG. 3, which shows $V_{2-3}$ (the DC voltage between the $LaCr_{0.85}Mg_{0.15}O_3$ and Pt electrodes) as a function of time. For both negative and positive applied currents, the introduction of 25 ppm $SO_2$ causes an increase in the magnitude of $V_{2-3}$ (i.e., in $|V_{2-3}|$). This increase disappears most rapidly upon the removal of $SO_2$ for applied current values of −0.15 and −0.2 mA. For the other values of applied current the behavior upon removal of $SO_2$ is not as rapid. The foregoing shows that there can be preferred signs and magnitudes for applied direct currents.

Example 3

Dependence of Response Magnitude on Concentration of $SO_2$

Figure 4:
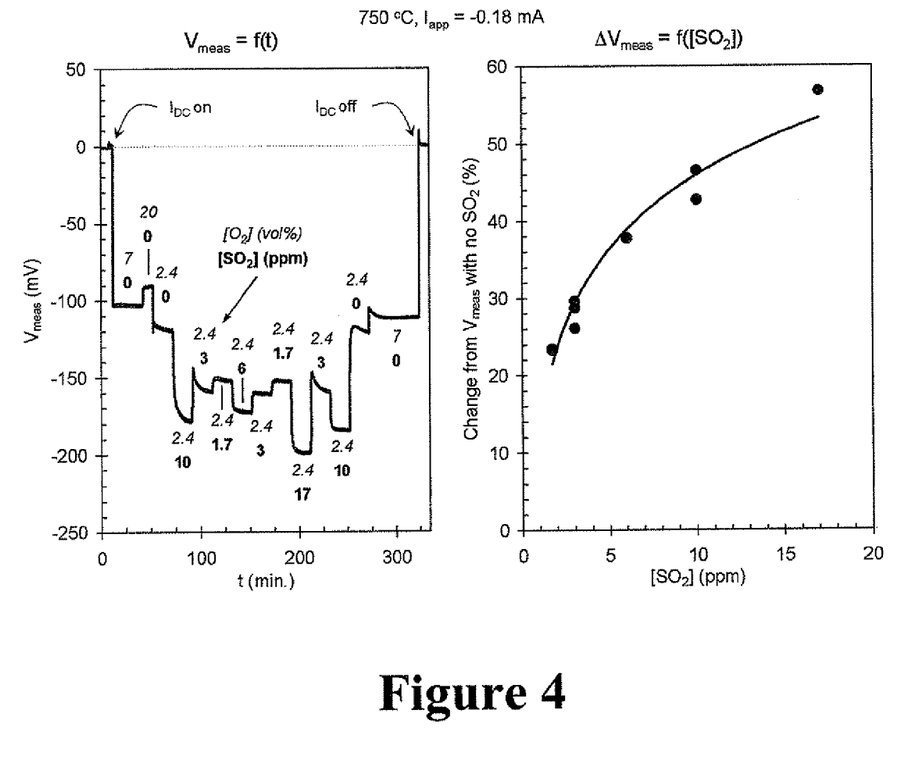
FIG. 4 Data showing variation of $V_{meas}$ as the $SO_2$ concentration ($[SO_2]$) is varied (left) and the changes in $V_{meas}$ as a function of $[SO_2]$ from 3-17 ppm (right). Operating temperature=750° C., $N_2$ used as balance gas.

The device of Example 2 was subjected to the following measurement procedure: At a temperature of 750° C. and with an $O_2$ concentration ($[O_2]$) of 7 vol %, −0.18 mA was applied between electrodes 1 and 2. $[O_2]$ was then changed to 20 vol %, then to 2.4 vol % and held there while the input concentration of $SO_2$ ($[SO_2]$) was varied between 3 and 17 ppm and then set to 0. $V_{2-3}$ was monitored throughout this series of gas concentration changes and the resultant data are shown in FIG. 4 wherein it is shown that the changes in $V_{2-3}$ are a single-valued, monotonically increasing function of $[SO_2]$ over the range 3-17 ppm. This function furnishes a mathematical relation between the amount of $SO_2$ in the mixture and the changes in $V_{2-3}$ and thus the measured change in $V_{2-3}$ can be used to infer the amount of $SO_2$ in a gas mixture containing an unknown amount of $SO_2$. The foregoing shows that the invention is useful for the quantitative detection (measurement) of $[SO_2]$ at high temperatures.

Example 4

Effect of Interfering Gases

Figure 5:
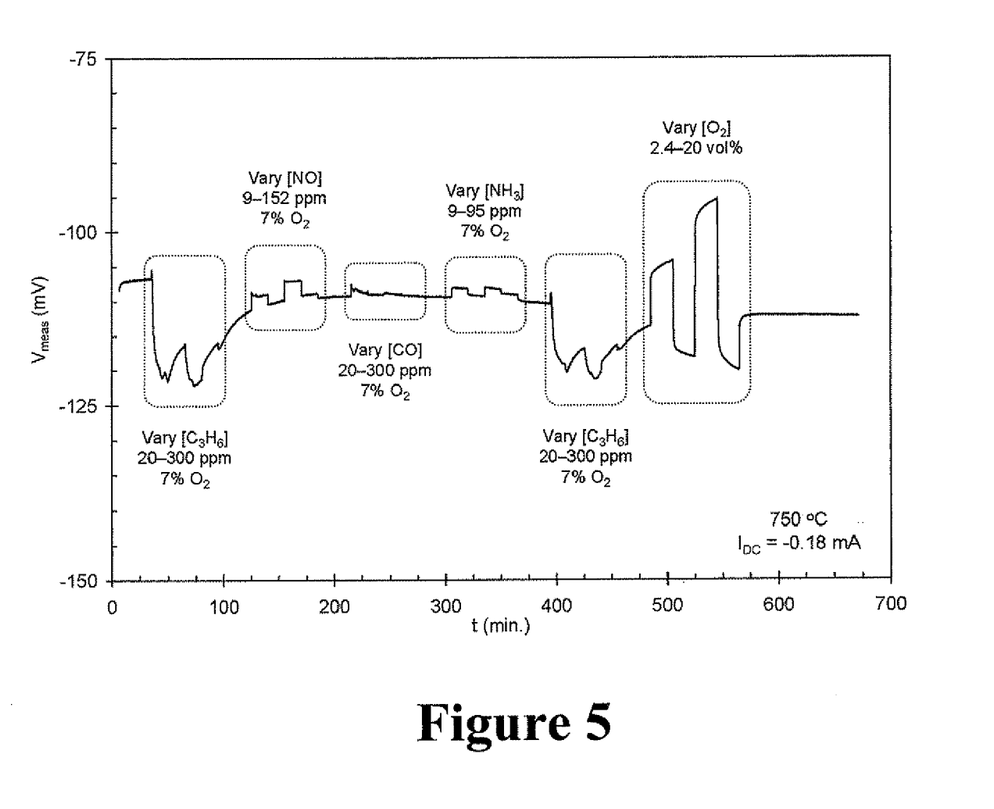
FIG. 5 Data showing effect of several possible interfering species, such as propylene ($C_3H_6$), nitric oxide (NO), carbon monoxide (CO), ammonia ($NH_3$), as well as varying $O_2$ concentration ($[O_2]$), on $V_{meas}$. Operating temperature=750° C., $N_2$ used as balance gas.

The device of Example 2 was subjected to the following measurement procedure: The temperature was held constant at 750° C., the $O_2$ concentration at 7 vol %, and $I_{DC}$ held constant at −0.18 mA. The concentration of propylene ($C_3H_6$) was varied between 20-300 ppm, then that of carbon monoxide (CO) between 20-300 ppm, then that of nitric oxide (NO) between 9-152 ppm, then that of ammonia ($NH_3$) between 9-95 ppm, then that of $C_3H_6$ again from 20-300 ppm and finally, the $O_2$ concentration was varied from 2.4-20 vol %. The resultant data are shown in FIG. 5. As shown, in comparison with FIG. 4, the changes in $V_{meas}$ induced by these species are small compared to the changes in $V_{meas}$ resulting from $SO_2$. The foregoing shows that the invention is relatively insensitive to some of the interfering species expected to coexist with $SO_2$ in combustion exhausts.

The description above focused on a first device constructed with Pt, $LaCr_{0.85}Mg_{0.15}O_3$, and $La_{0.6}Sr_{0.4}Co_{0.2}Fe_{0.8}O_3$ electrodes operated at a temperature of 750° C., and a second device constructed with Pt, $LaCr_{0.85}Mg_{0.15}O_3$, and $LaCr_{0.98}O_3$ electrodes operated at a temperature of 900° C. However, operation of a device with the geometry shown in FIG. 1 has been demonstrated with other combinations of electrode materials at other temperatures.

While there have been shown and described what are at present considered the preferred embodiments of the invention, it will be obvious to those skilled in the art that various changes and modifications can be prepared therein without departing from the scope of the inventions defined by the appended claims.

What is claimed is:

1. A method for selectively detecting gaseous sulfur dioxide in a $SO_2$-containing sample having a temperature of at least 500° C., the method comprising:
   (i) providing a $SO_2$-detecting device comprising an oxygen ion-conducting substrate having on its surface at least three electrodes comprising a first, second, and third electrode, the electrodes being constructed of thermally stable, electrically conductive materials and separated by a suitable space and in electrical communication by virtue of the oxygen ion-conducting substrate;
   (ii) driving a starting current of specified magnitude and temporal variation between the first and second electrodes;
   (iii) contacting the $SO_2$-detecting device with the $SO_2$-containing sample while maintaining the magnitude and any temporal variation of the starting current, wherein said $SO_2$-containing sample causes a change in the electrical conductance of said device; and
   (iv) detecting said change in the electrical conductance of said device based on measuring a specified electrical property related to or indicative of the conductance of the device between the first and third electrodes, or between the second and third electrodes, and detecting $SO_2$ in the $SO_2$-containing sample based on the measured change in electrical conductance.

2. The method according to claim 1, wherein the specified electrical property is voltage.

3. The method according to claim 1, wherein detection of $SO_2$ is based on a difference in a first and second measurement of the specified electrical property, wherein the first measurement is taken before the $SO_2$-detecting device is contacted with the $SO_2$-containing sample and while the starting current is being maintained between the first and second electrodes, and the second measurement is taken while contacting the $SO_2$-detecting device with the $SO_2$-containing sample while the magnitude of the starting current is being maintained between the first and second electrodes.

4. The method according to claim 1, wherein the current is maintained by a current-regulating device in electrical communication with the first and second electrodes.

5. The method according to claim 1, further comprising preheating the $SO_2$-detecting device, before contacting the device with the $SO_2$-containing sample, to a temperature capable of preventing condensation of vapors on the electrodes when the device is contacted with the $SO_2$-containing sample.

6. The method according to claim 5, wherein the $SO_2$-detecting device is preheated to a temperature of at least the temperature of the $SO_2$-containing sample.

7. The method according to claim 1, wherein the oxygen ion-conducting substrate material is a yttria-stabilized zirconia.

8. The method according to claim 7, wherein the yttria-stabilized zirconia is according to the formula $Zr_{0.84}Y_{0.08}O_{1.92}$.

9. The method according to claim 1, wherein the first and second electrodes are independently comprised of a composition within the formula $Ln_{1-y}A_yM_{1-z}M'_zO_{3-\delta}$ wherein Ln represents a lanthanide metal or scandium-group metal, A represents an alkaline earth metal, M represents a first row transition metal, and M' represents either a first row transition metal or an alkaline earth metal, wherein $0 \leq y \leq 0.4$, $0 \leq z \leq 1$, and $\delta$ represents an incremental variable of about 0 to about 0.5.

10. The method according to claim 9, wherein one or both of the first and second electrodes are comprised of a composition having the formula $La_{1-y}A_yM_{1-z}M'_zO_{3-\delta}$ wherein La represents lanthanum, A represents an alkaline earth metal, and M and M' each independently represents a first row transition metal, wherein $0 \leq y \leq 0.4$, $0 \leq z \leq 1$, and $\delta$ represents an incremental variable of about 0 to about 0.5.

11. The method according to claim 10, wherein one or both of the first and second electrodes are comprised of a composition having the formula $La_{0.6}Sr_{0.4}Co_{0.2}Fe_{0.8}O_{3-\delta}$.

12. The method according to claim 9, wherein one or both of the first and second electrodes are comprised of a composition having the formula $LaM_{1-z}M'_zO_{3-\delta}$ wherein La represents lanthanum, M represents a first row transition metal, M' represents an alkaline earth metal, $0 \leq z \leq 1$, and $\delta$ represents an incremental variable of about 0 to about 0.5.

13. The method according to claim 12, wherein one or both of the first and second electrodes are comprised of a composition having the formula $LaCr_{0.85}Mg_{0.15}O_{3-\delta}$.

14. The method according to claim 9, wherein the first electrode is comprised of a composition having the formula $La_{1-y}A_yM_{1-z}M'_zO_{3-\delta}$ wherein La represents lanthanum, A represents an alkaline earth metal, and M and M' each independently represents a first row transition metal, wherein $0 \leq y \leq 0.4$, $0 \leq z \leq 1$, and $\delta$ represents an incremental variable of about 0 to about 0.5, and the second electrode is comprised of a composition having the formula $LaM_{1-z}M'_zO_{3-\delta}$ wherein M represents a first row transition metal, and M' represents an alkaline earth metal, wherein $0 \leq y \leq 0.4$, $0 \leq z \leq 1$, and $\delta$ represents an incremental variable of about 0 to about 0.5.

15. The method according to claim 14, wherein the first electrode is comprised of a composition having the formula $La_{0.6}Sr_{0.4}Co_{0.2}Fe_{0.8}O_{3-\delta}$ and the second electrode is comprised of a composition having the formula $LaCr_{0.85}Mg_{0.15}O_{3-\delta}$.

16. The method according to claim 1, wherein the third electrode is comprised of platinum.

17. The method according to claim 1, wherein the first electrode is comprised of a composition having the formula $La_{0.6}Sr_{0.4}Co_{0.2}Fe_{0.8}O_{3-\delta}$, the second electrode is comprised of a composition having the formula $LaCr_{0.85}Mg_{0.15}O_{3-\delta}$, and the third electrode is comprised of platinum.

18. The method according to claim 1, wherein the first electrode is comprised of a composition having the formula $La_{0.8}Sr_{0.2}MnO_{3-\delta}$, the second electrode is comprised of a composition having the formula $La_{0.8}Sr_{0.2}FeO_{3-\delta}$, and the third electrode comprised of platinum.

19. The method according to claim 1, wherein the electrodes are coplanar.

20. The method of claim 1, wherein the $SO_2$-containing sample contains one or more chemical species in addition to $SO_2$.

21. The method of claim 1, wherein the device is operable at a temperature of at least 700° C.

22. The method of claim 1, wherein the device is operable at a temperature of at least 750° C.

23. The method of claim 1, wherein the device is operable at a temperature of at least 800° C.

24. A method for selectively detecting gaseous sulfur dioxide in a $SO_2$-containing sample having a temperature of at least 500° C., the method comprising:
  (i) preheating a $SO_2$-detecting device to a temperature of at least the temperature of the $SO_2$-containing sample, the $SO_2$-detecting device comprising an oxygen ion-conducting substrate material having on its surface at least three electrodes comprising a first, second, and third electrode, the electrodes being constructed of thermally stable, electrically conductive materials and separated by a suitable space and in electrical communication by virtue of the oxygen ion-conducting substrate;
  (ii) driving a starting current of specified magnitude and temporal variation between the first and second electrodes, before the $SO_2$-detecting device is contacted with the $SO_2$-containing sample, by a current-regulating device in electrical communication with said first and second electrodes, and recording a first measurement of an electrical property related to or indicative of the conductance of the device between the first and third or second and third electrodes by an electronic measuring device capable of measuring the electrical property, the electronic measuring device in electrical communication with said first and third or second and third electrodes during measurement;
  (iii) contacting the $SO_2$-detecting device with the $SO_2$-containing sample, and maintaining the magnitude and any temporal variation of the starting current by means of the current-regulating device which maintains the magnitude of the starting current while electrical resistance of the $SO_2$-detecting device changes due to contact with $SO_2$, while observing a second measurement of the electrical property by means of the electronic measuring device; and
  (iv) detecting $SO_2$ in the $SO_2$-containing sample based on a difference in the first and second measurements of the electrical property.

25. The method according to claim 24, wherein the electrical property related to or indicative of the conductance of the device being measured is a voltage, and the device measuring this property is a voltmeter.

26. A $SO_2$-detecting device capable of detecting $SO_2$ at a temperature of at least 500° C., the device comprising, an oxygen ion-conducting substrate material having on its surface at least three electrodes comprising a first, second, and third electrode, the electrodes constructed of thermally stable, electrically conductive materials and being separated by a suitable space and in electrical communication by virtue of the oxygen ion-conducting substrate.

27. The device of claim 26, wherein the first and second electrodes are independently comprised of a conductive oxide material, and the third electrode is comprised of a noble metal or noble metal alloy.

28. The device of claim 26, further comprising one or more electrical components that induce and regulate a current between the first and second electrodes.

29. The device of claim 26, further comprising one or more electrical components that measure an electrical property related to or indicative of the conductance of the device between the first and third, or second and third electrodes.

30. The device according to claim 29, wherein the one or more electrical components includes a voltmeter and the electrical property is voltage.

31. The device according to claim 26, wherein the oxygen ion-conducting substrate material is a yttria-stabilized zirconia.

32. The device according to claim 31, wherein the yttria-stabilized zirconia is according to the formula $Zr_{0.84}Y_{0.08}O_{1.92}$.

33. The device according to claim 26, wherein the first and second electrodes are independently comprised of a composition within the formula $Ln_{1-y}A_yM_{1-z}M'_zO_{3-\delta}$ wherein Ln represents a lanthanide or scandium-group metal, A represents an alkaline earth metal, M represents a first row transition metal, and M' represents either a first row transition metal or an alkaline earth metal, wherein $0 \leq y \leq 0.4$, $0 \leq z \leq 1$, and $\delta$ represents an incremental variable of about 0 to about 0.5.

34. The device according to claim 33, wherein one or both of the first and second electrodes are comprised of a composition having the formula $La_{1-y}A_yM_{1-z}M'_zO_{3-\delta}$ wherein La represents lanthanum, A represents an alkaline earth metal, and M and M' each independently represents a first row transition metal, wherein $0 \leq y \leq 0.4$, $0 \leq z \leq 1$, and $\delta$ represents an incremental variable of about 0 to about 0.5.

35. The device according to claim 34, wherein one or both of the first and second electrodes are comprised of a composition having the formula $La_{0.6}Sr_{0.4}Co_{0.2}Fe_{0.8}O_{3-\delta}$.

36. The device according to claim 33, wherein one or both of the first and second electrodes are comprised of a composition having the formula $LaM_{1-z}M'_zO_{3-\delta}$ wherein La represents lanthanum, M represents a first row transition metal, M' represents an alkaline earth metal, $0 \leq z \leq 1$, and $\delta$ represents an incremental variable of about 0 to about 0.5.

37. The device according to claim 36, wherein one or both of the first and second electrodes are comprised of a composition having the formula $LaCr_{0.85}Mg_{0.15}O_{3-\delta}$.

38. The device according to claim 33, wherein the first electrode is comprised of a composition having the formula $La_{1-y}A_yM_{1-z}M'_zO_{3-\delta}$ wherein La represents lanthanum, A represents an alkaline earth metal, and M and M' each independently represents a first row transition metal, wherein $0 \leq y \leq 0.4$, $0 \leq z \leq 1$, and $\delta$ represents an incremental variable of about 0 to about 0.5, and the second electrode is comprised of a composition having the formula $LaM_{1-z}M'_zO_{3-\delta}$ wherein M represents a first row transition metal, and M' represents an alkaline earth metal, wherein $0 \leq y \leq 0.4$, $0 \leq z \leq 1$, and $\delta$ represents an incremental variable of about 0 to about 0.5.

39. The device according to claim 38, wherein the first electrode is comprised of a composition having the formula $La_{0.6}Sr_{0.4}Co_{0.2}Fe_{0.8}O_{3-\delta}$ and the second electrode is comprised of a composition having the formula $LaCr_{0.85}Mg_{0.15}O_{3-\delta}$.

40. The device according to claim 26, wherein the third electrode is comprised of platinum.

41. The device according to claim 26, wherein the first electrode is comprised of a composition having the formula $La_{0.6}Sr_{0.4}Co_{0.2}Fe_{0.8}O_{3-\delta}$, the second electrode is comprised of a composition having the formula $LaCr_{0.85}Mg_{0.15}O_{3-\delta}$, and the third electrode is comprised of platinum.

42. The device according to claim 26, wherein the first electrode is comprised of a composition having the formula $La_{0.8}Sr_{0.2}MnO_{3-\delta}$, the second electrode is comprised of a composition having the formula $La_{0.8}Sr_{0.2}FeO_{3-\delta}$, and the third electrode comprised of platinum.

43. The device according to claim 26, wherein the electrodes are coplanar.

44. The device according to claim 26, wherein the device operates at a temperature of at least 750° C.

* * * * *